United States Patent [19]

Lightfoot

[11] Patent Number: 5,779,362

[45] Date of Patent: Jul. 14, 1998

[54] APPARATUS AND METHOD OF DETERMINING A CHARACTERISTIC RELATED TO THE THERMAL POWER OF A SAMPLE

[76] Inventor: John Adrian Lightfoot, Hill House, Hunter Rise, Beckermet, Cumbria CA21 2YP, United Kingdom

[21] Appl. No.: 501,941

[22] Filed: Jul. 13, 1995

[30] Foreign Application Priority Data

Jul. 15, 1994 [GB] United Kingdom ............... 9414364

[51] Int. Cl.$^6$ ................................................ G01F 17/00
[52] U.S. Cl. ........................... 374/33; 374/31; 374/32; 374/36
[58] Field of Search ........................... 374/31, 32, 33, 374/36, 102

[56] References Cited

U.S. PATENT DOCUMENTS 3,718,437  2/1973  Paloniemi ............................ 374/33 X

FOREIGN PATENT DOCUMENTS 2316072   10/1974  Germany.
9306616.3  6/1993  Germany.

OTHER PUBLICATIONS

Freer, K.M., "Design and Testing of a Calorimeter for Measurement of Plutonium Bearing Waste," Master of Science Degree (Thesis), University of Salford, Department of Electronic and Electrical Engineering, 1991.

Primary Examiner—William L. Oen
Assistant Examiner—Joseph L. Felber
Attorney, Agent, or Firm—Fish & Richardson, P.C.

[57] ABSTRACT

A calorimeter is disclosed comprising a sample chamber (12) adapted to enclose a sample, a thermally conductive reference surface (14) surrounding and insulated from the sample chamber (12) and a casing (16) surrounding and insulated from the reference surface. Temperature transducers, in communication with a micro-computer, record the temperatures of the sample chamber (VS) and reference surface (V1) at periodic intervals. The micro-computer is programmed to calculate the theoretical temperature (VT) of the sample chamber from the measured values of the temperature of the reference surface (V1) and estimated values of the thermal power of the sample (I), the thermal resistance from the sample to the sample chamber (RS) and the thermal capacity of the sample (CS), and to optimize the fit between the theoretical calculations (VT) and the corresponding measured values (VS) of the temperature of the sample chamber. A simplex form of optimization may be used to arrive at the optimum value of, inter alia, the thermal power (I) of the sample, the quantity which is to be indirectly measured.

22 Claims, 1 Drawing Sheet

APPARATUS AND METHOD OF DETERMINING A CHARACTERISTIC RELATED TO THE THERMAL POWER OF A SAMPLE

BACKGROUND OF THE INVENTION

This invention relates to calorimeters, and is concerned particularly, although not exclusively, with calorimeters which may be used to measure for example, the plutonium content of calcium fluoride slag. Such calorimeters measure thermal power and thus indirectly measure plutonium content by virtue of the heating effect of the alpha emissions from the plutonium.

In a conventional calorimeter, the sample is placed in a measurement chamber which is surrounded by and insulated from a surface which is held at a constant, reference temperature. This isothermal surface must be held at a known temperature to a high degree of accuracy, for example +/−0.001° C. The quality of the measurement depends directly upon the control of this temperature.

The way in which the measurement is taken is as follows. The temperature of the measurement chamber is allowed to rise, as a result of the heating effect of the sample, until the heat lost through the insulation to the isothermal surface equals the heat output by the sample. At equilibrium we can say:

$$\text{Thermal power} = \frac{\text{Temperature rise of sample chamber}}{\text{Thermal resistance of insulation}}$$

If the sample to be measured is of large thermal mass and its thermal power is small then the combination of large thermal capacity and high thermal insulation causes the time taken to reach equilibrium to be long. A typical time scale is about 4 days. However, a technique has been developed which allows the measurement to be made in about 1 day.

Clearly, for accurate measurement, the isotopic composition of the plutonium must be known, as the energy associated with the radioactive emissions from the various isotopes of plutonium differ widely.

It has been proposed to use the conventional calorimeter with a computer model to reduce the measurement time of samples. The temperature of the measurement chamber is recorded at regular intervals from the moment the sample is placed in the chamber, well before it has reached equilibrium. The parameters of the computer model are then adjusted until the temperatures for the chamber, predicted by the model, equal the measured temperatures to within an acceptable error. One of the parameters which is adjusted is the power output of the sample. The quality of the result depends on the accuracy of the model and the number of temperature measurements which are included in the optimization process. Acceptable results are obtained in 25% of the time taken for a conventional measurement.

The equations for the system are as follows:

$$CT \cdot \frac{dVT}{dt} + \frac{(VT-V1)}{RT} + \frac{(VT-VS)}{RS} = 0$$

$$CS \cdot \frac{dVS}{dt} + \frac{(VS-VT)}{RS} - I = 0$$

Where:
VT is the temperature of the sample chamber
VS is the temperature of the sample
V1 is the temperature of the reference surface
RT is the thermal resistance from sample chamber to reference surface
RS is the thermal resistance from sample to sample chamber
CT is the thermal capacity of the sample chamber
CS is the thermal capacity of the sample
I is the thermal power of the sample.

These can be solved ("Design and testing of a calorimeter for the measurement of plutonium-bearing waste", K. Freer, MSc Thesis, University of Salford, 1990) to give an equation of the form:

$$VT(t) = A + B \cdot e^{(-Ct)} + D \cdot e^{(-Et)}$$

Where:

$$A = V1 + RT \cdot I$$

$$B = \frac{(VT_0 - A)(q + 2pr) - 2 \cdot RS \cdot CS \cdot V1 - 2 \cdot RT(CT \cdot VT_0 + CS \cdot VS_0) + 2 \cdot A \cdot q}{4 \cdot p \cdot r}$$

$$C = \frac{q}{2 \cdot p} + r$$

$$D = VT_0 - A - B$$

$$E = \frac{q}{2 \cdot p} - r$$

$$p = RS \cdot RT \cdot CS \cdot CT$$

$$q = RS \cdot CS + RT \cdot CS + RT \cdot CT$$

$$r = \sqrt{\frac{q^2}{4 \cdot p^2} - \frac{1}{p}}$$

the subscript 0 indicates the value at time t=0.

The solution of the equations reduces the number of unknowns to 3 and greatly increases the chances of optimizing the model's parameters using the measured data. The unknowns are now I,RS and CS.

The measurement is made by recording the temperature of the sample chamber, as a function of time, after the sample has been introduced. The data is then used to perform a non-linear least squares fit, by optimizing the unknowns I, CS and RS in the equation:

$$\text{Residual} = \sum_i (VT_i(\text{calculated}) - VT_i(\text{measured}))^2$$

The simplex method may be used to perform the optimization and is described in "Numerical Recipes—The Art of Scientific Computing", W. H. Press et al., Cambridge University Press, 1986.

An essential feature of the calorimeter described above is the isothermal surface. This is maintained at a constant temperature by heaters on the top, bottom and side of the surface. Each is driven separately by a power supply and all three are controlled by a computer. The temperatures are measured by arrays of thermistors connected to a digital voltmeter by a scanner. The calorimeter cannot be used until the isothermal surface is at its operating temperature. This takes several days for a large calorimeter.

The present invention seeks to eliminate the need for the temperature controlled surface.

SUMMARY OF THE INVENTION

Accordingly, the present invention provides a calorimeter comprising a sample chamber adapted to enclose a sample; a reference surface surrounding and insulated from the sample chamber; means for measuring the temperature of the sample chamber and the reference surface; and means for determining a characteristic of a sample enclosed within the sample chamber which is functionally related to its thermal power in dependence upon the time variation of the measurements obtained.

Since the calorimeter is designed to take account of time variations of the temperature of the reference surface, no control system is required and the reference surface is not required to reach its operating temperature. Such a calorimeter could be transported to a new site and used immediately. The only electronics required are, for example, a scanner to select the various temperature sensors, a digital voltmeter to measure the temperatures and a computer to process the results.

The reference surface still exists. Its temperature is not controlled, but is allowed to float and is simply measured. It is preferred that the surface be spatially isothermal but its temperature may vary with time. Thus, the reference surface is preferably formed from thermally conductive material.

To enable the time variations of the temperatures to be accurately determined, it is preferred that the means for measuring the temperature of the sample chamber and the reference surface includes means for recording the two temperatures at periodic intervals.

To enable the determination of the said characteristic of the sample, it is preferred that means be provided for approximately calculating the theoretical temperature of the sample chamber from the measured values of the temperature of the reference surface and estimated values of the said characteristic of the sample, the thermal resistance from the sample to the sample chamber and the thermal capacity of the sample and optimizing the fit between the approximate theoretical calculations and the corresponding measured values of the temperature of the sample chamber.

As will become clear, the means for approximately calculating the theoretical temperature of the sample chamber preferably includes means for approximately evaluating the following integrals:

$$Q_1(t) = H \cdot e^{-X \cdot t} \int_0^t V1(\lambda) \cdot e^{X \cdot \lambda} \, d\lambda$$

$$Q_2(t) = J \cdot e^{-Y \cdot t} \int_0^t V1(\lambda) \cdot e^{Y \cdot \lambda} \, d\lambda$$

Where:

$$H = \frac{CS \cdot RS \sqrt{(q^2 - 4 \cdot p)} - 2 \cdot p + q \cdot RS \cdot CS}{2p \sqrt{(q^2 - 4 \cdot p)}}$$

$$J = \frac{CS \cdot RS \sqrt{(q^2 - 4 \cdot p)} + 2 \cdot p - q \cdot RS \cdot CS}{2p \sqrt{(q^2 - 4 \cdot p)}}$$

$$X = \frac{q + \sqrt{(q^2 - 4 \cdot p)}}{2 \cdot p}$$

$$Y = \frac{q - \sqrt{(q^2 - 4 \cdot p)}}{2 \cdot p}$$

$$p = RS \cdot RT \cdot CS \cdot CT$$

$$q = RS \cdot CS + RT \cdot CS + RT \cdot CT$$

RT is the thermal resistance from sample chamber to reference surface

CT is the thermal capacity of the sample chamber

RS is an estimate of the thermal resistance from the sample to the sample chamber CS is an estimate of the thermal capacity of the sample.

The means for approximately evaluating integrals of the form:

$$I_{t_m} = K \cdot e^{-L \cdot t_m} \int_0^{t_m} V1(\lambda) \cdot e^{L \cdot \lambda} \, d\lambda$$

may utilize the relationship:

$$I_{t_m} = K \int_{t_{m-1}}^{t_m} V1(\lambda) \cdot e^{L(\lambda - t_m)} \, d\lambda + (I_{t_{m-1}} \cdot e^{L(t_{m-1} - t_m)})$$

so as to improve the accuracy of numerical integration, if that is the evaluation procedure adopted. The means for approximately evaluating the integrals may include means for numerically calculating the integrals using Laplace's difference equation.

Where the said characteristic of the sample is its thermal power, to arrive at a theoretical value for the temperature of the sample chamber, the means for approximately calculating the theoretical temperature of the sample chamber preferably includes means for approximately evaluating the equation:

$$Q_3(t) = RT \cdot I + F e^{-X \cdot t} + G e^{-Y \cdot t} + Q_1(t) + Q_2(t)$$

Where F and G are respectively given by:

$$\frac{\sqrt{(q^2 - 4 \cdot p)} \; (VT_0 - RT \cdot I) - 2 \cdot RT \cdot CS \cdot VS_0 - 2 \cdot RT \cdot CT \cdot VT_0 + q \cdot VT_0 + RT \cdot I \cdot q}{2 \sqrt{(q^2 - 4p)}}$$

$$\frac{\sqrt{(q^2 - 4 \cdot p)} \; (VT_0 - RT \cdot I) + 2 \cdot RT \cdot CS \cdot VS_0 + 2 \cdot RT \cdot CT \cdot VT_0 - q \cdot VT_0 - RT \cdot I \cdot q}{2 \sqrt{(q^2 - 4 \cdot p)}}$$

I is an estimate of the thermal power of the sample the subscript 0 indicates the value at time t=0.

The means for determining the thermal power of the sample preferably includes means for selecting values of CS, RS and I which, when used in calculating the values of $Q_3(t)$ give an optimum fit between the values of $Q_3(t)$ and the corresponding measured values of VT.

The optimum values of CS, RS and I may be selected by the simplex method.

To guard against excess heat loss and mechanical shock, the reference surface is preferably in turn surrounded by a casing.

The present invention also extends to a method of determining a characteristic of a sample which is functionally related to its thermal power comprising enclosing the sample within a sample chamber, the sample chamber being surrounded by and insulated from a reference surface; periodically measuring the temperature of the sample chamber and the reference surface; and determining the said characteristic of the sample in dependence upon the time variation of the measurements obtained.

Preferably, the temperature of the reference surface is allowed to vary with time in dependence upon heat transfer to and from the sample chamber and the external environment. Preferably again, the reference surface is maintained spatially isothermal.

The said characteristic of the sample may be, for example, its plutonium content, its chemical composition or any other quantity functionally dependent upon thermal power, such as thermal power itself. Any of these quantities may be evaluated once any other is known, provided that sufficient additional information is also known which permits the relevant functional relationships to be evaluated.

DETAILED DESCRIPTION OF THE INVENTION

Figure 1:
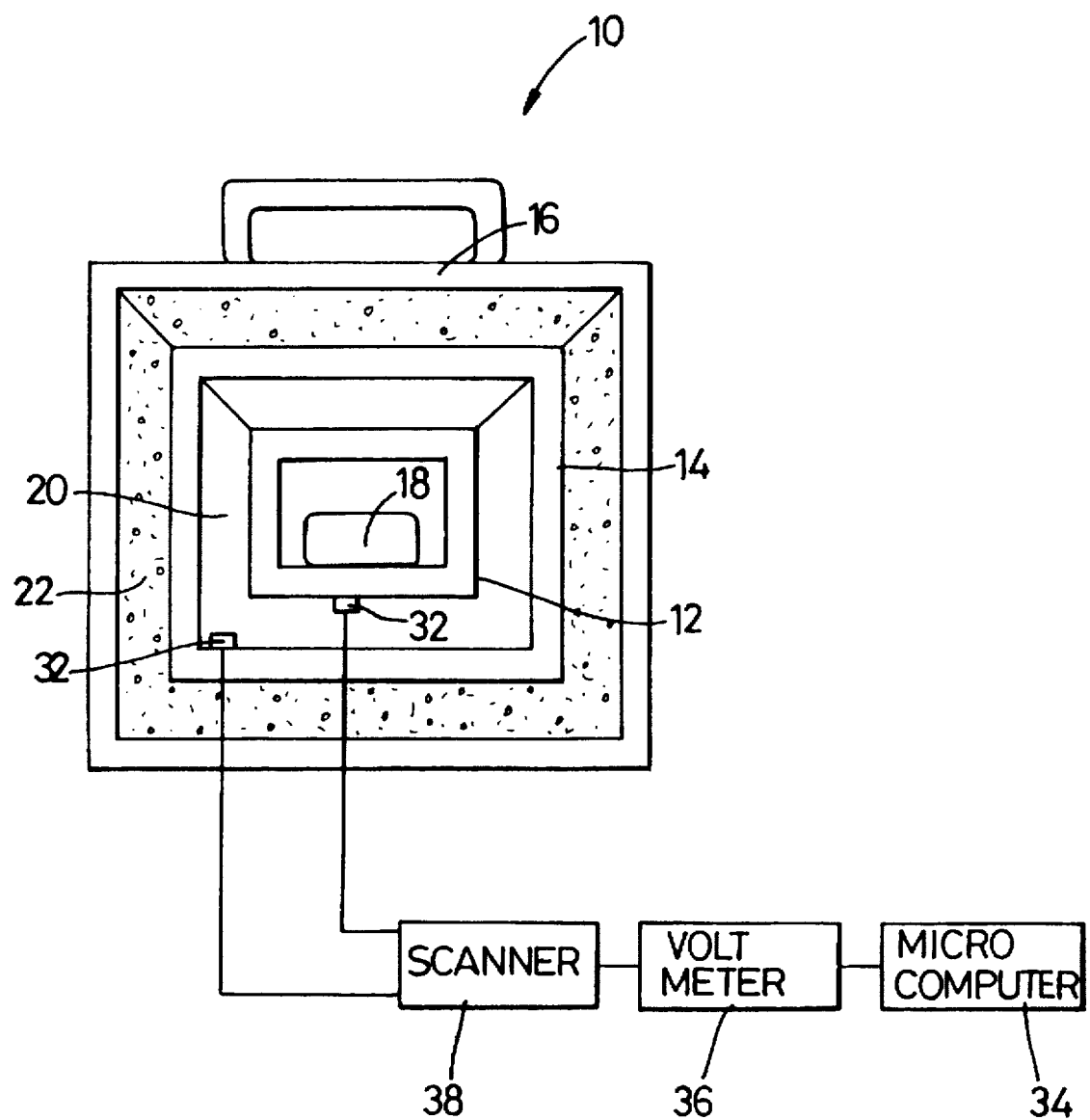
FIG. 1 is a diagrammatic illustration of a calorimeter in accordance with the present invention.

As can be seen from FIG. 1, the calorimeter 10 consists of three nested containers 12, 14, 16. The innermost chamber is the sample chamber 12, into which a sample 18 is placed when the calorimeter is to be used. The sample 18 gives up thermal energy in the form of alpha radiation, which is absorbed by the sample chamber 12, raising the temperature of the chamber 12.

Surrounding the sample chamber 12 and separated from it by an insulating barrier 20 is the middle container 14, which serves as the reference surface of the calorimeter. The reference surface is formed from a thermally conductive metallic material such as stainless steel or aluminium, as are all three containers 12, 14, 16. Where the calorimeter is constructed in such a way that one dimension is substantially larger than the other two, e.g. in the form of a long cylinder, then the chambers and surfaces 12, 14, 16 need not be closed in the sense of having bases and lids. So long as the ends of the cylinders are sufficiently well insulated, end effects arising from the open-ended cylinders are negligible. The term "surrounding" will be understood accordingly and does not require the various chambers to encapsulate one another completely.

Surrounding the reference surface 14 is, in turn, a casing 16, separated from the reference surface by thermal insulation 22, such as structural foam. Where samples of high thermal power are to be used, the insulation may be relatively conductive, e.g. copper wire, to prevent the build-up of heat in the sample chamber. The thermal resistivity of the insulation will be chosen depending upon the expected thermal power of the sample.

Temperature transducers, such as thermistors 32, are arranged on the sample chamber surface and on the reference surface to measure the requisite temperatures and the data obtained is periodically sampled by a micro-computer 34 via the medium of a digital voltmeter 36 and a scanner 38. The micro-computer is suitably programmed to carry out the calculations explained below.

The effects of the varying temperature of the reference surface are included in the calculation. Since the calculation accommodates a reference surface with a variable temperature, no time is needed for the calorimeter to reach its operating temperature and the amount of associated electronics is reduced considerably.

The equations for the system are the same as those given for the fixed-temperature reference surface, but provision must be made in solving them for the temperature variation. The solution is now of the form:

$$VT(t) = Q_3(t)$$

$Q_3(t)$ being as defined above.

This is similar to the fixed-temperature solution, but now includes two definite integrals $Q_1(t)$ and $Q_2(t)$, which are functions of the temperature of the reference surface. This temperature is not a known function but it is measured and the integrals can be performed numerically. This is achieved by using Laplace's difference equation:

$$\int_{x_0}^{x_1} f(x) \cdot dx = h \left[ f_0 + \frac{1}{2} \Delta f_0 - \frac{1}{12} \Delta^2 f_0 + \frac{1}{24} \Delta^3 f_0 \ldots \right]$$

Where:
h is the sample period
$\Delta$ is the forward difference operator

There are practical difficulties in evaluating the integrals by computer. When t becomes large the exponential terms become either very large or very small and can cause mathematical over- or under-flow. This problem can be avoided by rearranging the integrals to be of the form:

$$I_{t_m} = K \cdot e^{-L \cdot t_m} \int_0^{t_m} V1(\lambda) \cdot e^{L \cdot \lambda} \cdot d\lambda$$

and utilizing the relationship:

$$I_{t_m} = K \int_{t_{m-1}}^{t_m} V1(\lambda) \cdot e^{L(\lambda - t_m)} \cdot d\lambda + (I_{t_{m-1}} \cdot e^{L(t_{m-1} - t_m)})$$

The exponentials are now calculated over one measurement interval rather than from t=0 thereby eliminating the difficulty. The values of $Q_3(t)$ can now be evaluated by computer and the simplex method can be used to minimise the residual between the calculated and measured values of the temperature of the sample chamber.

The concept of a calorimeter with no temperature controlled surfaces has been shown to work. The temperature transient produced when the sample is placed in the measurement chamber can be used to calculate the heat output of the sample when there is no fixed reference temperature. A calorimeter can be built which has no heaters or computer controlled power supplied and requires little time to set up and operate. Practical measurements of the power output of samples are possible in a fraction (25%) of the time a conventional calorimeter would take to reach equilibrium.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A calorimeter comprising:
   a sample chamber adapted to enclose a sample;
   a reference surface surrounding and insulated from the sample chamber;

means for measuring the temperature of the sample chamber and the reference surface;

means for determining a characteristic functionally related to the thermal power of a sample enclosed within the sample chamber from the time variation of the temperature measurements obtained, the determining means including means for calculating the approximate theoretical temperature of the sample chamber from:
  i) the measured values of the reference surface temperature,
  ii) the estimated values of the said characteristic of the sample,
  iii) the thermal resistance from the sample to the sample chamber, and
  iv) the thermal capacity of the sample; and means for optimizing the fit between the approximate theoretical calculations and the corresponding measured values of the temperature of the sample chamber.

2. A calorimeter according to claim 1 in which the reference surface is thermally conductive.

3. A calorimeter according to claim 1 or claim 2 in which the means for measuring the temperature of the sample chamber and the reference surface includes means for recording the two temperatures at periodic intervals.

4. A calorimeter according to claim 1 in which the means for calculating the approximate theoretical temperature of the sample chamber includes means for approximately evaluating the following integrals:

$$Q_1(t) = H \cdot e^{-X \cdot t} \int_0^t V1(\lambda) \cdot e^{X \cdot \lambda} \, d\lambda$$

$$Q_2(t) = J \cdot e^{-Y \cdot t} \int_0^t V1(\lambda) \cdot e^{Y \cdot \lambda} \, d\lambda$$

where:

$$H = \frac{CS \cdot RS \sqrt{(q^2 - 4 \cdot p)} - 2 \cdot p + q \cdot RS \cdot CS}{2p \sqrt{(q^2 - 4 \cdot p)}}$$

$$J = \frac{CS \cdot RS \sqrt{(q^2 - 4 \cdot p)} + 2 \cdot p - q \cdot RS \cdot CS}{2p \sqrt{(q^2 - 4 \cdot p)}}$$

$$X = \frac{q + \sqrt{(q^2 - 4 \cdot p)}}{2 \cdot p}$$

$$Y = \frac{q - \sqrt{(q^2 - 4 \cdot p)}}{2 \cdot p}$$

$$p = RS \cdot RT \cdot CS \cdot CT$$

$$q = RS \cdot CS + RT \cdot CS + RT \cdot CT$$

RT is the thermal resistance from sample chamber to reference surface

CT is the thermal capacity of the sample chamber

RS is an estimate of the thermal resistance from the sample to the sample chamber t is the time V1 is the temperature of the reference surface CS is an estimate of the thermal capacity of the sample.

5. A calorimeter according to claim 4 in which the means for approximately evaluating integrals of the form:

$$I_{t_m} = K \cdot e^{-L \cdot t_m} \int_0^{t_m} V1(\lambda) \cdot e^{L \cdot \lambda} \, d\lambda$$

utilizes the relationship:

$$I_{t_m} = K \int_{t_{m-1}}^{t_m} V1(\lambda) \cdot e^{L(\lambda - t_m)} \, d\lambda + (I_{t_{m-1}} \cdot e^{L(t_{m-1} - t_m)}).$$

6. A calorimeter according to claim 4 or claim 5 in which the means for approximately evaluating the integrals includes means for numerically calculating the integrals using Laplace's difference equation.

7. A calorimeter according to claim 6 in which said characteristic of the sample is its thermal power and the means for calculating the approximate theoretical temperature of the sample chamber includes means for approximately evaluating the equation:

$$Q_3(t) = RT \cdot I + Fe^{-X \cdot t} + Ge^{-Y \cdot t} + Q_1(t) + Q_2(t)$$

where F and G are respectively given by:

$$\frac{\sqrt{(q^2 - 4 \cdot p)} \ (VT_0 - RT \cdot I) - 2 \cdot RT \cdot CS \cdot VS_0 - 2 \cdot RT \cdot CT \cdot VT_0 + q \cdot VT_0 + RT \cdot I \cdot q}{2 \sqrt{(q^2 - 4p)}}$$

$$\frac{\sqrt{(q^2 - 4 \cdot p)} \ (VT_0 - RT \cdot I) + 2 \cdot RT \cdot CS \cdot VS_0 + 2 \cdot RT \cdot CT \cdot VT_0 - q \cdot VT_0 - RT \cdot I \cdot q}{2 \sqrt{(q^2 - 4 \cdot p)}}$$

I is an estimate of the thermal power of the sample the subscript 0 indicates the value at time t=0.

8. A calorimeter according to claim 7 in which the means for determining the thermal power of the sample includes means for selecting values of CS, RS and I which when used in calculating the values of $Q_3(t)$ give an optimum fit between the values of $Q_3(t)$ and the corresponding measured values of VT.

9. A calorimeter according to claim 8 in which the optimum values of CS, RS and I are selected by the simplex method.

10. A calorimeter according to claim 1 in which the reference surface is in turn surrounded by a casing.

11. A calorimeter according to claims 1 or 2 in which the reference surface is nonisothermal.

12. A calorimeter according to claim 3 in which the reference surface is nonisothermal.

13. A method of determining a characteristic functionally related to the thermal power of a sample, comprising:

enclosing the sample within a sample chamber, the sample chamber being surrounded by and insulated from a reference surface;

measuring the temperature of the sample chamber and the reference surface;

determining the characteristic from the time variation of the temperature measurements obtained, the method including the calculating of the approximate theoretical temperature of the sample chamber from:
  i) the measured values of the reference surface temperature,
  ii) the estimated values of the said characteristic of the sample, iii) the thermal resistance from the sample to the sample chamber, and iv) the thermal capacity of the sample; and optimizing the fit between the approximate theoretical calculations and the corresponding measured values of the temperature of the sample chamber.

14. A method according to claim 13 in which the temperature of the reference surface is allowed to vary with time in dependence upon heat transfer to and from the sample chamber and the external environment.

15. A method according to claim 13 or claim 14 in which the reference surface is maintained spatially isothermal.

16. A method according to claim 15 in which the reference surface is thermally conductive.

17. A method according to claim 12 in which the calculation of the approximate theoretical temperature of the sample chamber includes approximately evaluating the following integrals:

$$Q_1(t) = H \cdot e^{-X \cdot t} \int_0^t V1(\lambda) \cdot e^{X \cdot \lambda} \cdot d\lambda$$

$$Q_2(t) = J \cdot e^{-Y \cdot t} \int_0^t V1(\lambda) \cdot e^{Y \cdot \lambda} \cdot d\lambda$$

where:

$$H = \frac{CS \cdot RS \sqrt{(q^2 - 4 \cdot p)} - 2 \cdot p + q \cdot RS \cdot CS}{2p \sqrt{(q^2 - 4 \cdot p)}}$$

$$J = \frac{CS \cdot RS \sqrt{(q^2 - 4 \cdot p)} + 2 \cdot p - q \cdot RS \cdot CS}{2p \sqrt{(q^2 - 4 \cdot p)}}$$

$$X = \frac{q + \sqrt{(q^2 - 4 \cdot p)}}{2 \cdot p}$$

$$Y = \frac{q - \sqrt{(q^2 - 4 \cdot p)}}{2 \cdot p}$$

$$p = RS \cdot RT \cdot CS \cdot CT$$

$$q = RS \cdot CS + RT \cdot CS + RT \cdot CT$$

RT is the thermal resistance from sample chamber to reference surface

CT is the thermal capacity of the sample chamber

RS is an estimate of the thermal resistance from the sample to the sample chamber t is the time V1 is the temperature of the reference surface CS is an estimate of the thermal capacity of the sample.

18. A method according to claim 17 in which the integrals of the form:

$$I_{t_m} = K \cdot e^{-L \cdot t_m} \int_0^{t_m} V1(\lambda) \cdot e^{L \cdot \lambda} \cdot d\lambda$$

are evaluated according to the relationship:

$$I_{t_m} = K \int_{t_{m-1}}^{t_m} V1(\lambda) \cdot e^{L(\lambda - t_m)} \cdot d\lambda + (I_{t_{m-1}} \cdot e^{L(t_{m-1} - t_m)}).$$

19. A method according to claim 17 or claim 18 in which the integrals are approximately evaluated by numerically calculation using Laplace's difference equation.

20. A method according to claim 17 in which said characteristic of the sample is its thermal power and the calculation of the approximate theoretical temperature of the sample chamber includes approximately evaluating the equation:

$$Q_3(t) = RT \cdot I + Fe^{-X \cdot t} + Ge^{-Y \cdot t} + Q_1(t) + Q_2(t)$$

where F and G are respectively given by:

$$\frac{\sqrt{(q^2 - 4 \cdot p)} \; (VT_0 - RT \cdot I) - 2 \cdot RT \cdot CS \cdot VS_0 - 2 \cdot RT \cdot CT \cdot VT_0 + q \cdot VT_0 + RT \cdot I \cdot q}{2\sqrt{(q^2 - 4p)}}$$

$$\frac{\sqrt{(q^2 - 4 \cdot p)} \; (VT_0 - RT \cdot I) + 2 \cdot RT \cdot CS \cdot VS_0 + 2 \cdot RT \cdot CT \cdot VT_0 - q \cdot VT_0 - RT \cdot I \cdot q}{2\sqrt{(q^2 - 4 \cdot p)}}$$

I is an estimate of the thermal power of the sample the subscript 0 indicates the value at time t=0.

21. A method according to claim 20 in which the thermal power of the sample is determined by selecting values of CS, RS and I which when used in calculating the values of $Q_3(t)$ give an optimum fit between the values of $Q_3(t)$ and the corresponding measured values of VT.

22. A method according to claim 21 in which the optimum values of CS, RS and I are selected by the simplex method.

* * * * *